(12) United States Patent
Cao et al.

(10) Patent No.: US 8,221,409 B2
(45) Date of Patent: Jul. 17, 2012

(54) THERMALLY INSULATED IRRIGATION CATHETER ASSEMBLY

(75) Inventors: Hong Cao, Savage, MN (US); Huisun Wang, Maple Grove, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 871 days.

(21) Appl. No.: 11/962,600

(22) Filed: Dec. 21, 2007

(65) Prior Publication Data
US 2009/0163911 A1    Jun. 25, 2009

(51) Int. Cl.
*A61B 18/14*    (2006.01)
(52) U.S. Cl. .......................................................... 606/41
(58) Field of Classification Search .................... 606/41, 606/48–50; 607/101–105
See application file for complete search history.

(56) References Cited

U.S. PATENT DOCUMENTS

| | | | |
|---|---|---|---|
| 5,056,517 A | 10/1991 | Fenici | |
| 5,230,349 A | 7/1993 | Langberg | |
| 5,334,193 A | 8/1994 | Nardella | |
| 5,348,554 A | 9/1994 | Imran et al. | |
| 5,423,811 A | 6/1995 | Imran et al. | |
| 5,462,521 A | 10/1995 | Brucker et al. | |
| 5,545,161 A | 8/1996 | Imran | |
| 5,643,197 A * | 7/1997 | Brucker et al. | ................. 604/20 |
| 5,658,278 A | 8/1997 | Imran et al. | |
| 5,697,927 A | 12/1997 | Imran et al. | |
| 5,792,140 A | 8/1998 | Tu et al. | |
| 5,843,152 A | 12/1998 | Tu et al. | |
| 5,893,884 A | 4/1999 | Tu | |
| 5,913,856 A | 6/1999 | Chia et al. | |
| 5,919,188 A | 7/1999 | Shearon et al. | |
| 6,002,956 A * | 12/1999 | Schaer | ......................... 600/381 |
| 6,015,407 A | 1/2000 | Rieb et al. | |
| 6,017,338 A | 1/2000 | Brucker et al. | |
| 6,120,476 A | 9/2000 | Fung et al. | |
| 6,162,219 A | 12/2000 | Nilsson et al. | |
| 6,171,275 B1 | 1/2001 | Webster, Jr. | |

(Continued)

FOREIGN PATENT DOCUMENTS
WO    2005/048858 A1    6/2005
(Continued)

OTHER PUBLICATIONS

Wittkampf, et al., Radiofrequency Ablation with a Cooled Porous Electrode Catheter, JACC vol. 11, No. 2, Feb. 1988: 17A Abstracts.

(Continued)

*Primary Examiner* — Michael Peffley
*Assistant Examiner* — Daniel Fowler
(74) *Attorney, Agent, or Firm* — Dykema Gossett PLLC

(57) ABSTRACT

The present invention relates to ablation electrode assemblies. The present invention further relates to an insulated irrigated ablation electrode assembly. The insulated irrigated ablation electrode assembly of the present invention includes a proximal member, a distal member and an intermediate thermally insulating member. The proximal member includes a body portion defined by an outer surface, an inner cavity defined within the outer body portion, and at least one passageway that extends from the inner cavity to the outer surface of the body portion. The distal member of the electrode assembly includes a distal end. Moreover, the intermediate member of the electrode assembly is disposed between the proximal member and the distal member thereby thermally insulating the proximal member from the distal member.

28 Claims, 4 Drawing Sheets

U.S. PATENT DOCUMENTS

| | | | |
|---|---|---|---|
| 6,217,576 B1 | 4/2001 | Tu et al. | |
| 6,363,937 B1 | 4/2002 | Hovda et al. | |
| 6,589,237 B2* | 7/2003 | Woloszko et al. | 606/41 |
| 6,602,242 B1 | 8/2003 | Fung et al. | |
| 6,611,699 B2* | 8/2003 | Messing | 600/372 |
| 6,662,034 B2* | 12/2003 | Segner et al. | 600/373 |
| 6,723,094 B1* | 4/2004 | Desinger | 606/50 |
| 6,942,661 B2 | 9/2005 | Swanson | |
| 7,166,105 B2 | 1/2007 | Mulier et al. | |
| 2002/0049438 A1* | 4/2002 | Sharkey et al. | 606/41 |
| 2003/0004506 A1* | 1/2003 | Messing | 606/41 |
| 2003/0097130 A1* | 5/2003 | Muller et al. | 606/41 |
| 2004/0092806 A1* | 5/2004 | Sagon et al. | 600/374 |
| 2004/0133197 A1* | 7/2004 | Utley et al. | 606/41 |
| 2004/0243121 A1* | 12/2004 | Lee et al. | 606/41 |
| 2005/0177151 A1* | 8/2005 | Coen et al. | 606/41 |
| 2006/0184165 A1* | 8/2006 | Webster et al. | 606/41 |
| 2006/0264925 A1* | 11/2006 | Sharareh et al. | 606/41 |
| 2007/0032788 A1* | 2/2007 | Edwards et al. | 606/41 |
| 2007/0156131 A1* | 7/2007 | Datta | 606/41 |
| 2007/0203551 A1* | 8/2007 | Cronin et al. | 607/101 |

FOREIGN PATENT DOCUMENTS

| | | |
|---|---|---|
| WO | 2007/136979 A2 | 11/2007 |

OTHER PUBLICATIONS

Wittkampf, et al., Saline-Irrigated Radiofrequency Ablation Electrode with External Cooling, Journal of Cardiovascular Electrophysiology, vol. 16, No. 3, Mar. 2005.

International Search Report and Written Opinion for PCT/US2008/084014 mailed Feb. 2, 2009.

Thomas, et al., A Comparison of Open Irrigated and Non-Irrigated Tip Catheter Ablation for Pulmonary Vein Isolation, Europace 6:330-335 (2004).

* cited by examiner

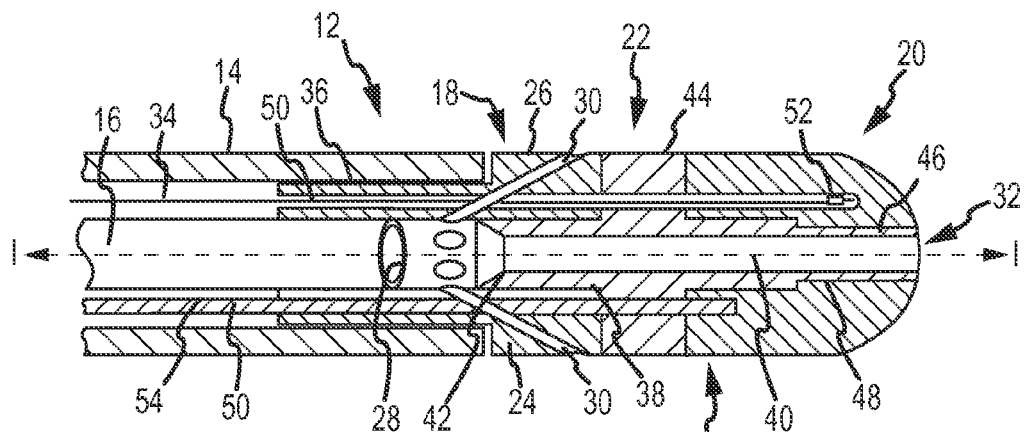
FIG.2
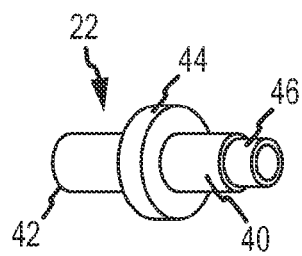
FIG.3
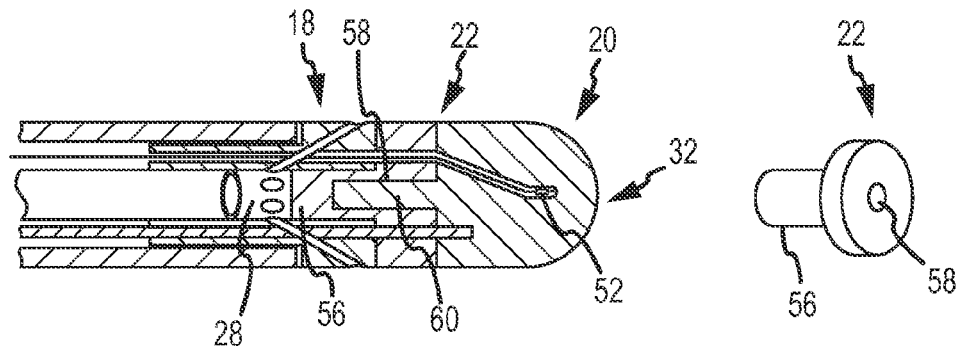 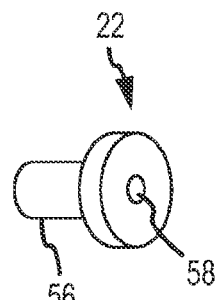
FIG.4  FIG.5
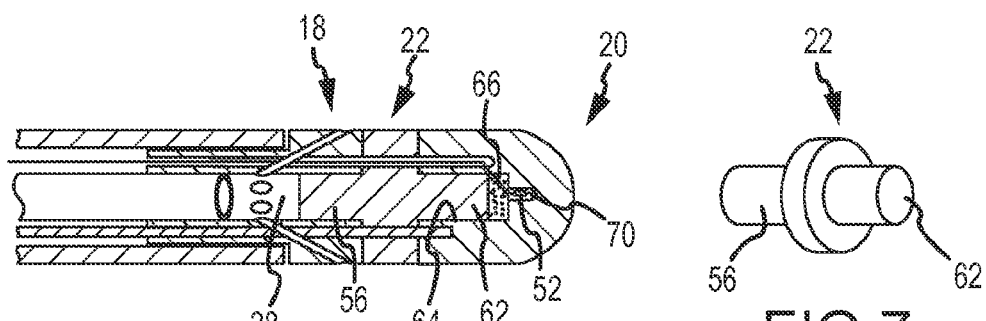 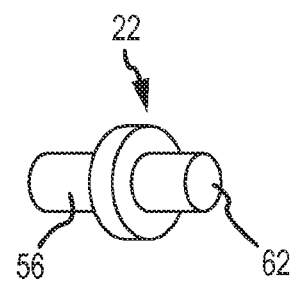
FIG.6  FIG.7

THERMALLY INSULATED IRRIGATION CATHETER ASSEMBLY

BACKGROUND OF THE INVENTION a. Field of the Invention

The instant invention relates to ablation electrode assemblies. The present invention further relates to ablation electrode assemblies having a mechanism for irrigating targeted areas. The present invention further relates to a thermally insulated irrigation ablation electrode assembly that includes an insulation member and/or insulation coating that thermally insulates the ablation electrode from the manifold which provides fluid irrigation and enhances the temperature response exhibited by the electrode assembly.

b. Background Art

Electrophysiology catheters have been used for an ever-growing number of procedures. For example, catheters have been used for diagnostic, therapeutic, and ablative procedures, to name just a few examples. Typically, a catheter is manipulated through the patient's vasculature and to the intended site, for example, a site within the patient's heart, and carries one or more electrodes, which may be used for ablation, diagnosis, or other treatments.

There are a number of methods used for ablation of desired areas, including for example, radiofrequency (RF) ablation. RF ablation is accomplished by transmission of radiofrequency energy to a desired target area through an electrode assembly to ablate tissue at the target site. Because RF ablation may generate significant heat, which if not controlled can result in excessive tissue damage, such as steam pop, tissue charring, and the like, it is desirable to include a mechanism to irrigate the target area and the device with biocompatible fluids, such as saline solution. The use of irrigated ablation catheters can also prevent the formation of soft thrombus and/or blood coagulation.

Typically, there are two classes of irrigated electrode catheters, open and closed irrigation catheters. Closed ablation catheters usually circulate a cooling fluid within the inner cavity of the electrode. Open ablation catheters typically deliver the cooling fluid through open outlets or openings on the surface of the electrode. Open ablation catheters use the inner cavity of the electrode, or distal member, as a manifold to distribute saline solution, or other irrigation fluids known to those skilled in the art, to one or more passageways that lead to openings/outlets provided on the surface of the electrode. The saline thus flows directly through the outlets of the passageways onto the distal electrode member. This direct flow of fluid through the distal electrode tip lowers the temperature of the distal tip during operation, rendering accurate monitoring and control of the ablative process more difficult. Accordingly, it is desirable to have a method that allows for cooling of the electrode while having accurate monitoring and control of the ablative process. In addition, due to the heat created by the ablation procedures and the direct contact of the irrigation member with the ablation electrode, the irrigation channels may have a tendency to overheat if the manifold is made of metal or any other thermally conductive material. As a result, the manifold or irrigation member has generally been made of a reduced thermally conductive material, such as for example, plastic or any other plastic-like material. Although the reduced thermally conductive manifold may be beneficial, plastic-like manifolds or irrigation members are generally difficult to machine in the proportions necessary for the use in catheter assemblies and the resulting structures may cause reliability issues. Moreover, a major drawback of an irrigation catheter is its lack of temperature response due to the fluid cooling of the ablation electrode.

Overall, open flush irrigated ablation catheters may improve the safety of RF catheter ablation by preventing protein aggregation and blood coagulation. In addition, in order to improve and/or maximize the effect of irrigation, it important to ensure that the irrigation fluid is able to effectively cool the electrode assembly, in particular, the ablation electrode, while at the same time effectively controlling the temperature response of the ablation electrode.

BRIEF SUMMARY OF THE INVENTION

The present invention relates to ablation electrode assemblies. The present invention further relates to an irrigated ablation electrode assembly that includes an intermediate member that serves as a thermally insulating member. The thermally insulating member is positioned between the distal member, i.e., for example, an ablation electrode and the proximal member that serves as a fluid irrigation manifold which irrigates the outer surface of the electrode assembly.

More particularly, the present invention relates to an electrode assembly for an irrigated ablation catheter assembly. The electrode assembly includes a proximal member having a body portion that defines an outer surface. An inner cavity is defined within the outer body portion of the proximal member. The proximal member further includes at least one passageway that extends from the inner cavity to the outer surface of the body portion. The electrode assembly further includes a distal member having a hemispherical end. The electrode assembly further includes an intermediate member disposed between the proximal member and the distal member. The intermediate member serves as a thermal insulating member which insulates the proximal member from the distal member of the electrode assembly therein preventing any contact between the proximal member and the distal member.

The present invention further relates to an electrode assembly for an irrigated ablation catheter assembly as previously described. In addition, the electrode assembly of the present invention further includes an insulation coating that may be disposed on the outer surface of the body portion of the proximal member. The insulation coating may further be disposed on an outer surface of the distal member of the electrode assembly.

The present invention further relates to an ablation catheter system including an irrigated ablation electrode assembly connected to a catheter shaft, therein forming an irrigated catheter assembly connected to an energy source and a fluid source.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 2 is a side cross-sectional view of an embodiment of the electrode assembly of the present invention;

FIG. 3 is an isometric view of an insulating intermediate member in accordance with the embodiment of the electrode assembly provided in FIG. 2;

FIG. 4 is a side cross-sectional view of an embodiment of the electrode assembly of the present invention;

FIG. 5 is an isometric view of an insulating intermediate member in accordance with the embodiment of the electrode assembly provided in FIG. 4;

FIG. 6 is a side cross-sectional view of an embodiment of the electrode assembly of the present invention;

FIG. 7 is an isometric view of an insulating member in accordance with the embodiment of the electrode assembly provided in FIG. 6;

DETAILED DESCRIPTION OF THE INVENTION

In general, the instant invention relates to irrigated ablation electrode assemblies and to methods of using the irrigated ablation electrode assemblies in connection with catheter assemblies. For purposes of this description, similar aspects among the various embodiments described herein will be referred to by the same reference number. As will be appreciated, however, the structure of the various aspects may be different among the various embodiments.

Figure 1:
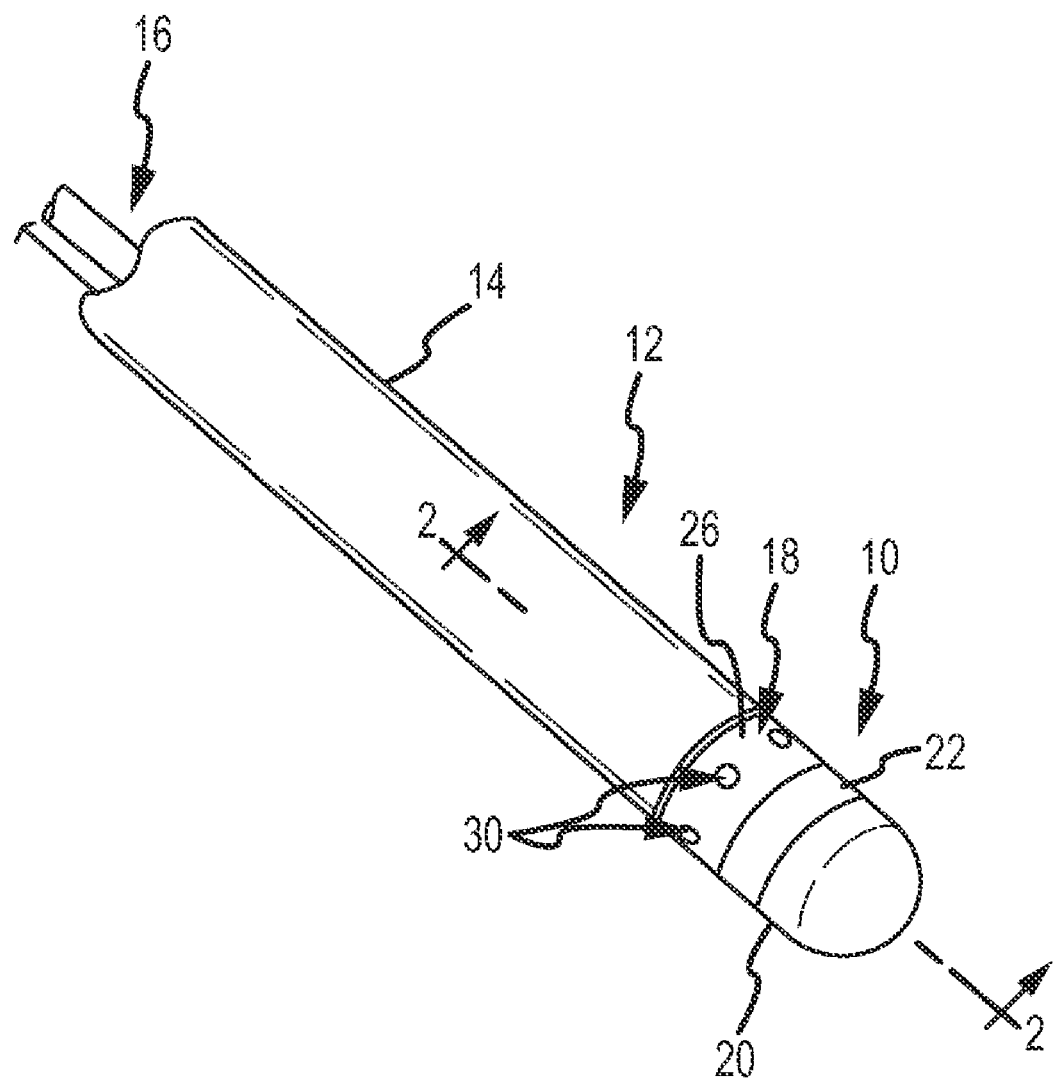
FIG. 1 is an isometric view of an thermally insulated irrigation ablation electrode assembly in accordance with one embodiment of the present invention.

As generally shown in the embodiment illustrated in FIG. 1, the ablation electrode assembly 10 may comprise part of an irrigation ablation catheter assembly 12. The present embodiments describe RF ablation electrodes and assemblies, but it is contemplated that the present invention is equally applicable to any number of other ablation electrodes and assemblies where the temperature of the device and the targeted tissue area may be factors during the procedure. FIGS. 2-11, discussed in more detail below, illustrate ablation electrode assemblies 10 according to alternate embodiments of the present invention.

In accordance with an embodiment, FIG. 1 is an isometric view of irrigated ablation electrode assembly 10 connected to a catheter shaft 14 as part of irrigated ablation catheter assembly 12. Catheter assembly 12 further includes at least one fluid delivery tube 16 for supplying fluid to electrode assembly 10.

As shown in FIG. 1, electrode assembly 10 is generally defined by proximal member 18, distal member 20, and intermediate member 22 positioned between proximal member 18 and distal member 20 serially, therein creating electrode assembly 10. In accordance with the present invention, intermediate member 22 serves as an insulation member comprised of thermally insulating material positioned between proximal member 18 and distal member 20.

In an embodiment, proximal member 18 includes a body portion 24 defined by an outer surface 26. As can be see in FIG. 2, proximal member 18 further includes an inner cavity 28 that may be coupled to or is in fluid communication with fluid delivery tube 16 of catheter assembly 12. Proximal member 18 further includes at least one fluid or irrigation passageway 30 that extends from inner cavity 28 to outer surface 26 of proximal member 18. Distal member 20 may be a generally cylindrical in shape. Distal member 20 may further include a distal end 32. Distal end 32 of distal member 20 may be hemispherical in shape. Electrode assembly 10 further includes intermediate member 22 disposed between proximal member 18 and distal member 20. Proximal member 18, intermediate member 22 and distal member 20 are serially coupled together or connected with one another along the same longitudinal axis (1) to form electrode assembly 10. Electrode assembly 10 is further connected to and/or coupled with catheter shaft 14 to form thermally insulated irrigation ablation catheter assembly 12. FIGS. 2-11 further provide various embodiments of the electrode assembly of the present invention.

Proximal member 18 of the present invention is comprised of a thermally and/or potentially electrically conductive material for delivery of irrigation fluid to outer surface 26 of proximal member 18 and the rest of the electrode assembly 10. Examples of electrically conductive material include gold, platinum, iridium, palladium, stainless steel, and mixtures thereof. In particular, a combination of platinum and iridium may be used in various combinations. In general, proximal member 18 comprised of an electrically conductive material, in particular metals, is currently much easier to machine and create than a manifold comprised of plastic or other non-thermally conductive material. Accordingly it is beneficial to have a metallic irrigation member wherein inner cavity 28 and passageways 30 may be more easily created either through machining, die casting, or any other method known by those of ordinary skill in the art. Moreover, in an embodiment, proximal member 18 may be or include a sensing electrode. In particular, upon attachment of a sensing wire (not shown) to proximal member 18, proximal member 18 may be used as an electrocardiogram (ECG) sensing electrode. In an embodiment, a pull wire (not shown) may be connected to or attached to proximal member 18 for controlling the movement and deflection catheter shaft 14.

As shown in FIG. 2, proximal member 18 may be configured to receive fluid delivery tube 16 carried within catheter assembly 12. In particular, fluid delivery tube 16 may be provided within a central inner lumen 34 provided within catheter shaft 14. Moreover, proximal member 18 may include a plurality of passageways 30. Proximal member 18, also referred to as a manifold, distributes fluid throughout and along the outer surface of electrode assembly 10, through the use of passageways 30. In particular, passageways 30 extend from inner cavity 28 toward the outer surface 26 of proximal member 18. In an embodiment, passageways 30 are oriented generally towards distal member 20 at an acute angle with respect to longitudinal axis (1) extending to outer surface 26 of proximal member 18. More specifically, passageways 30 may be either straight or curved towards outer surface 26 of proximal member 18. In an embodiment, a plurality of passageways 30 are substantially equally distributed around proximal member 18 to provide substantially equal distribution of fluid to the targeted tissue area and/or the outside of electrode assembly 10. Proximal member 18 may be configured to provide a single, annular passageway 30, or a number of individual passageways 30 equally distributed around the proximal member 18. Moreover, passageways 30 may be generally tubular and may have a constant diameter along the length of the passageway. Alternate configurations having various diameters along all or portions of the length of the passageways may be used.

As further shown in FIG. 2, at least one passageway 30 may extend towards distal member 20, in particular to outer surface 26 of proximal member 18, at an angle ($\Theta$) less than 90 degrees from the central longitudinal axis (1) of electrode assembly 10. In an embodiment, passageways 30 extends at an angle ($\Theta$) between about 20 to about 70 degrees, and for some embodiments, between about 30 to about 65 degrees. Moreover, passageways 30 are angled by varying degrees depending on the design of electrode assembly 10. Such design variations may include, for example, but are not limited to, the varying lengths of outer surface 26 of proximal member 18, the length of intermediate member 22 and distal member 20, as well as the overall diameter of electrode assembly 10. Alternate positions and angles of the passageway(s) 30 may be provided in alternate embodiments of electrode assembly 10 as recognized by those of ordinary skill in the art. In an embodiment, passageways 30 may have a diameter ranging in size from approximately 0.008 to approximately 0.015 inches, and for some embodiment between approximately 0.010 to approximately 0.012 inches.

Proximal member 18 may further include a mounting portion 36 for coupling and/or connecting proximal member 18 with catheter shaft 14. In an embodiment, inner cavity 28 of proximal member may receive portion 38 of intermediate member 22 for connecting and/or coupling the two members, 18, 22, together. In an embodiment, intermediate member 22 may provide an axial distal passageway 40 that extends from inner cavity 28 of proximal member 18 to distal end 32 of distal member 20. As can be seen in FIG. 2, distal passageway 40 enables irrigation fluid to flow to distal end 32 of distal member 20 therein substantially irrigating the tip of electrode assembly 10. Moreover, in an embodiment, proximal end 42 of intermediate member 22 is tapered and/or angled such that the diameter of axial passageway 40 is less than the diameter of inner cavity 28 of proximal member 18. Similarly, the distal end of inner cavity 28 may be tapered providing the same configuration, depending on the design and manufacturing of members 18, 22.

Intermediate member 22, also referred to as insulation member, is generally comprised of a thermally nonconductive or reduced thermally conductive material that serves to insulate the irrigation fluid, as well as separate proximal member 18 and distal member 20 from physically coming in contact with one another. Moreover, intermediate member 22 may comprise an electrically nonconductive material. In general, intermediate member 22 is lower in thermal conductivity, and preferably substantially lower, than distal member 20. In an embodiment, intermediate member 22 is made from a reduced thermally conductive polymer. A reduced thermally conductive material is one with physical attributes that decrease heat transfer by about 10% or more, provided that the remaining structural components are selected with the appropriate characteristics and sensitivities to maintain adequate monitoring and control of the process. One reduced thermally conductive material may include polyether ether ketone ("PEEK"). Further examples of non or reduced thermally conductive materials useful in conjunction with the present invention include, but are not limited to, HDPE, polyimide thermoplastic resins, such as those provided by General Electric Plastics (now known as SABIC Innovative Plastics) under the trademark ULTEM®, polyaryletherketones, polyetheretherketones, polyurethane, polypropylene, oriented polypropylene, polyethylene, crystallized polyethylene terephthalate, polyethylene terephthalate, polyester, polyetherimide, acetyl, ceramics, and various combinations thereof. In an embodiment, intermediate member may further be selected from other plastic materials, such as silicone or polyether block amides such as those sold under the trademark PEBAX® and generally available from Arkema France.

In an embodiment, intermediate member 22 includes an outer surface 44 that may provide substantially 1 millimeter of spacing between proximal member 18 and distal member 20. In an embodiment, this length of outer surface 44 may vary depending on the design of electrode assembly 10 and in order to achieve predesired spacing of distal member 20 relative to catheter 14 and proximal member 18. Outer surface 44 is aligned with outer surface 26 of proximal member 18 such that a substantially smooth transition is provided between the two surfaces. Accordingly, proximal member 18 and intermediate member 22 have substantially the same diameter. Of course, various modifications in alternate embodiments may be provided as recognized by one of ordinary skill in the art. An embodiment of intermediate member 22, which is provided as part of electrode assembly 10 shown in FIG. 2, is more fully shown in FIG. 3. In an embodiment, as shown, the thermally insulating intermediate member 22 may further include a distal portion 46 that has a diameter less than the remaining portions of intermediate member 22. In an embodiment, as shown in FIG. 2, distal passageway 40 may include a diameter that is substantially equal throughout the length of intermediate member 22. In an alternate embodiment, distal passageway 40 may include an overall diameter that varies along the length of intermediate member 22; in particular, the diameter of distal passageway 40 may decrease towards distal end 32 of distal member 20.

In an embodiment, distal member 20 is generally comprised of any electrically, and potentially thermally, conductive material known to those of ordinary skill in the art for delivery of ablative energy to target tissue areas. Accordingly, in an embodiment, distal member 20 is an ablation electrode for use in RF ablation. Examples of electrically conductive material include gold, platinum, iridium, palladium, stainless steel, and any mixtures thereof. In particular, a combination of platinum and iridium may be used in various combinations. Overall, distal member 20 of ablation electrode assembly 10 may have a generally cylindrical shape terminating in distal end 32, such as, for example, a partially spherical or hemispherical distal end.

In an embodiment, as shown in FIG. 2, distal member 20 may further include an irrigation channel 48 that extends through distal member 20 to distal end 32, therein providing an outlet or opening on the end surface of distal member 20. As shown in FIG. 2, a portion of distal passageway 40 of intermediate member 22 is received within irrigation channel 48 of distal member 20. Accordingly, the fluid passed through distal passageway 40 during irrigation of electrode assembly 10 is thermally insulated from distal member 20. There is no direct contact between distal member 20, the ablation electrode, and proximal member 18 which serves to distribute irrigation fluid within fluid electrode assembly 10. Therefore, during ablation, distal member 20 is not directly cooled by the irrigated fluid provided by proximal member 18 and therefore can be used to measure the temperature of the tissue (such as, for example, endocardial surface) for accurate temperature monitoring (by the temperature sensor 52). It is recognized that some peripheral cooling of distal member 20 may be accomplished through the positioning of passageways 30, 40. Distal member 20 and intermediate member 22 may be connected or coupled together by any known mechanism including adhesives, press-fit configurations, snap-fit configurations, or any other mechanism known to one of ordinary skill in the art.

Additional components, such as those known in the art, may be integrated and/or incorporated into electrode assembly 10 of the type disclosed by the present invention, and as shown by various embodiments. Accordingly, multiple lumens 50 may be provided throughout electrode assembly 10 for slidably receiving additional components. For example, distal member 20 of electrode 10 may further include at least one temperature sensing mechanism 52, such as a thermal sensor, disposed therein for measurement and temperature control/regulation of electrode assembly 10. The temperature sensing mechanism(s) 52 can be any mechanism known to one of skill in the art, including for example, thermocouples or thermistors. In an embodiment, the temperature sensing mechanism 52 may further be surrounded, or encapsulated, by a second thermally conductive and electrically non-conductive material (not shown). The thermally conductive and electrically non-conductive material may serve to hold temperature sensing mechanism 52 in place within distal member 20 and provide improved heat exchange between temperature sensing mechanism 52 and distal member 20. This material may be comprised of a number of materials known to one of ordinary skill in the art, including for example, thermally conductive resins, epoxies, or potting compounds. A power wire 54 may further be provided within distal member 20 of electrode assembly 10. Both the thermal sensor 52 and power wire 54 extend through lumens 50 provided within the catheter assembly 12, such as, for example, through the proximal member 18, into intermediate member 22 and ultimately into distal member 20 of electrode assembly 10.

An alternate embodiment of the present invention, as shown in FIGS. 4 and 5, provides an intermediate member 22 that includes proximal portion 56 that is coupled to and/or connected with inner cavity 28 of proximal member. Intermediate member 22 further provides coupling cavity 58 that receives mounting member 60 provided by distal member 20. Mounting member 60 of distal member 20 is received within coupling cavity 58 therein securely connecting distal member 20 with intermediate member 22. As previously described the coupling with and/or connecting together of proximal member 18, intermediate member 22 and distal member 20 may be accomplished by various methods known by one of ordinary skill in the art. In accordance with this embodiment of the present invention, thermal sensor 52 is provided within distal member 20 and substantially along the central longitudinal axis of electrode assembly 10.

An alternate embodiment of the present invention, as shown in FIGS. 6 and 7, provides an intermediate member 22 that includes proximal portion 56 that is coupled to and/or connected with inner cavity 28 of proximal member and a distal portion 62 that is received within cavity 64 of distal member 20. Thermal sensor 52 is provided within a thermal cavity 70 positioned at approximately the center of distal member 20 along the central longitudinal axis. Upon insertion of thermal sensor 52 in thermal cavity 70, an adhesive or other bonding material 66 may be provided to ensure that thermal sensor 52 is relatively secure in position and distal portion 62 is slidably received within cavity 64 of distal member 20. As a result, thermal sensor 52 is fixed in position by adhesive/bonding material 66, thereby securing distal portion 62 within cavity 64.

Figure 8:
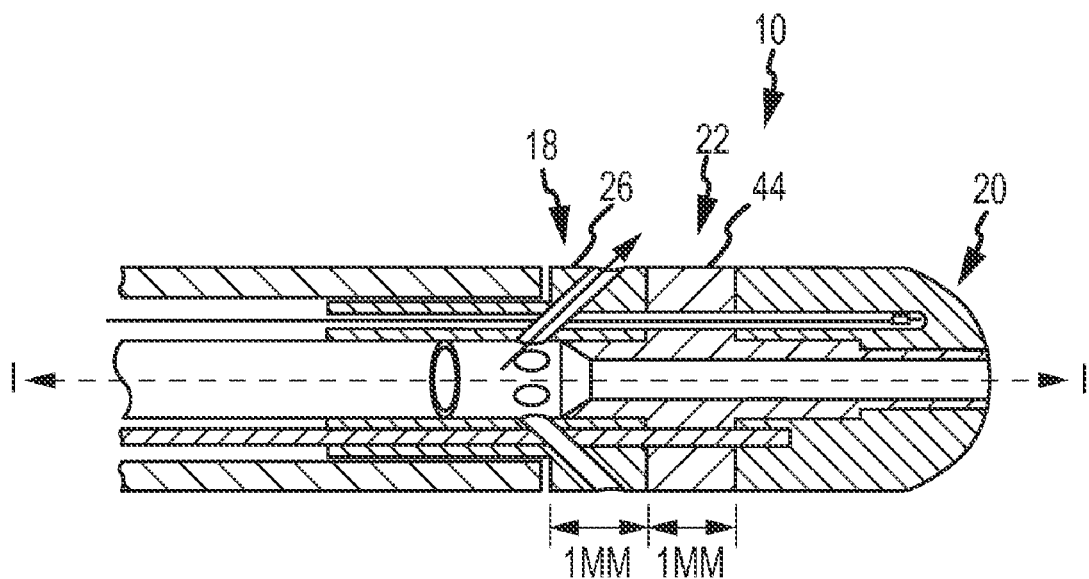
FIG. 8 is a side cross-section view of an alternate embodiment of the present invention.

As shown in FIG. 8, an alternate embodiment of the present invention as shown in FIG. 1 is further provided, wherein the length of outer surface 26 of proximal member 18 is approximately 1 millimeter (1 mm) and outer surface 44 of intermediate member 22 is approximately 1 millimeter (1 mm). In order to effectively cool distal member 20, such as, for example, a 2.5 millimeter ablation electrode, and meet the catheter requirements, such as, for example, having a 1 millimeter sensing electrode provided by proximal member 18, it is necessary to achieve a 1 millimeter spacing for proximal member 18 and intermediate member 22, respectively. As can be seen in FIG. 8, in order to ensure that outer surface 26 of proximal member 18 is limited to 1 millimeter, passageway 30 is provided at a greater angle in relation to the central longitudinal axis (1) of electrode assembly 10. This larger angle deteriorates the fluid cooling to the ablation electrode and makes it less effective.

Figure 9:
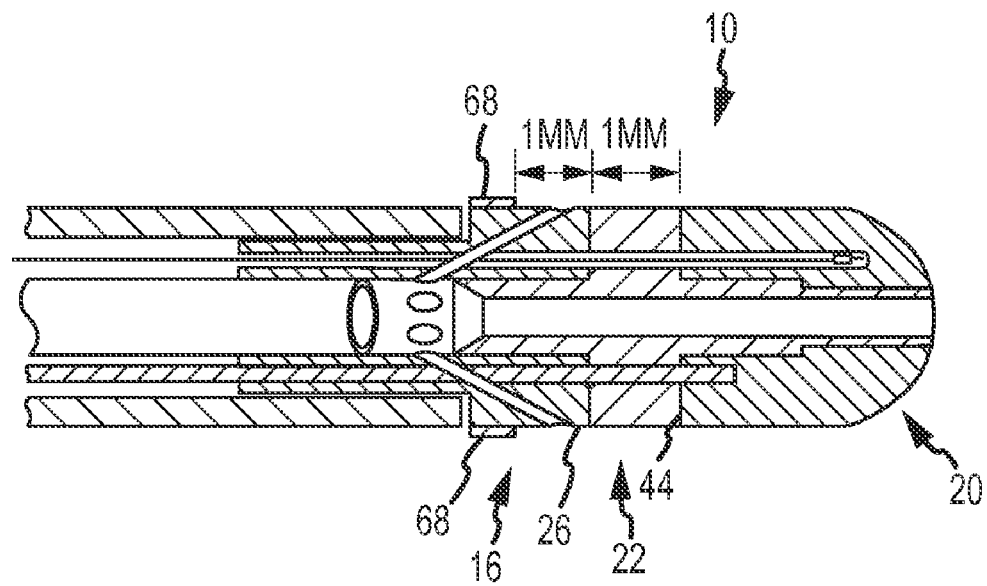
FIG. 9 is a side cross-section view of an alternate embodiment of the present invention.

Accordingly, an embodiment of the present invention, as seen in FIG. 9, further includes an electrically insulation coating 68 disposed on outer surface 26 of proximal member 18. Electrical insulation coating 68 is disposed on outer surface 26 in order to modify the outer length of proximal member 18 that may further be configured to comprise and/or include a sensing electrode through the connection of a sensing wire (not shown) to proximal member 18. According to the embodiment, the electrical insulation coating 68 may be disposed on the proximal portion of outer surface 26 so that the exposed part of proximal member 18 may have a length of approximately 1 millimeter as a sensing electrode. Overall proximal member 18 may include an increased outer surface length ranging from 1.5-2.5 millimeters, therein reducing the angle of passageway 30 in relation to the central longitudinal axis of electrode assembly 10. The addition of electrical insulation coating 68 allows for a more effective irrigation flow through reduced angled passageways, while at the same time meeting the requirements of catheter assembly 12, such as provided a 1 millimeter sensing electrode and a 1 millimeter spacing between proximal member 18 and distal member 20.

In general, electrical insulation coating 68 may be comprised of an electrically non-active material known by one of ordinary skill in the art. In particular, insulation coating 68 may be comprised of diamond, diamond-like-carbon (DLC) or polytetrafluoroethylene (PTFE) which is commonly sold by the E.I. du Pont de Nemours and Company under the trademark TEFLON®, or combinations therefore. In an embodiment, electrical insulation coating 68 is provided along the entire circumference of proximal member 18. The length of electrical insulation coating 68 may vary depending on the length of outer surface 26 of proximal member 18 and any other relative requirements of electrode assembly 10 or catheter assembly 12.

Figure 10:
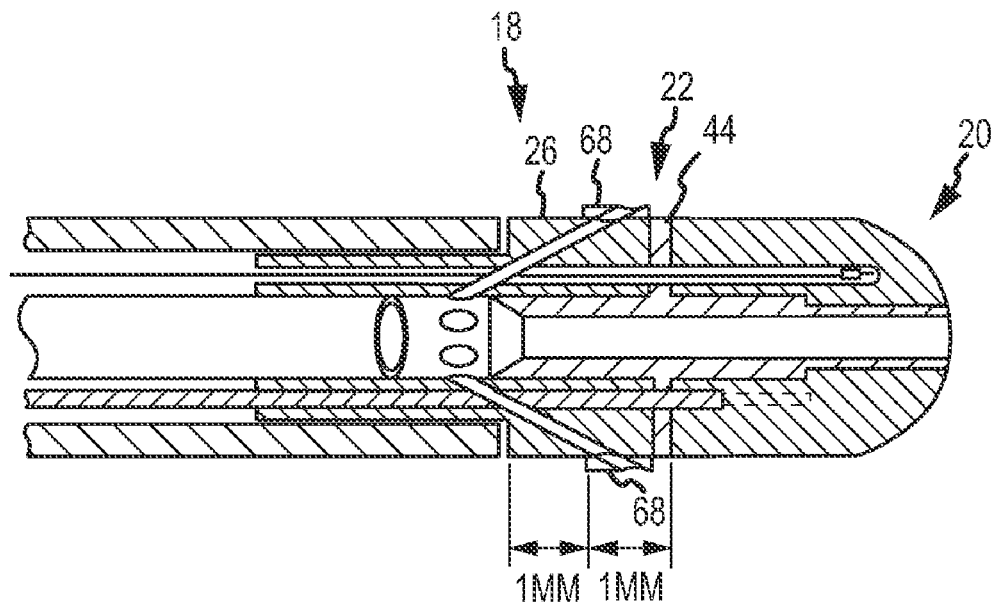
FIG. 10 is a side cross-section view of an alternate embodiment of the present invention.

FIG. 10 further provides an alternate embodiment wherein electrical insulation coating 68 is disposed on the distal portion of outer surface 26 of proximal member 18. Moreover, with the addition of electrical insulation coating 68, the outer surface 44 of intermediate member 22 may be reduced. Accordingly, the thickness of intermediate member 22, as reflected by the length of outer surface 44, may be reduced to 0.5 millimeters in size or less to achieve effective insulating between distal member 20 and proximal member 18. As a result, irrigation passageway 30 as provided by proximal member 18, may be located in closer proximity to distal member 20 therein providing more effective cooling of distal member 20. As shown in FIG. 10, the combined non-conductive length of electrical insulation coating 68 with outer surface 44 of intermediate member 22 meets the electrode spacing requirement therein providing a 1 millimeter sensing electrode, as well as 1 millimeter in length spacing between the sensing electrode provided by proximal member 18 and the ablation electrode provided by distal member 20.

Figure 11:
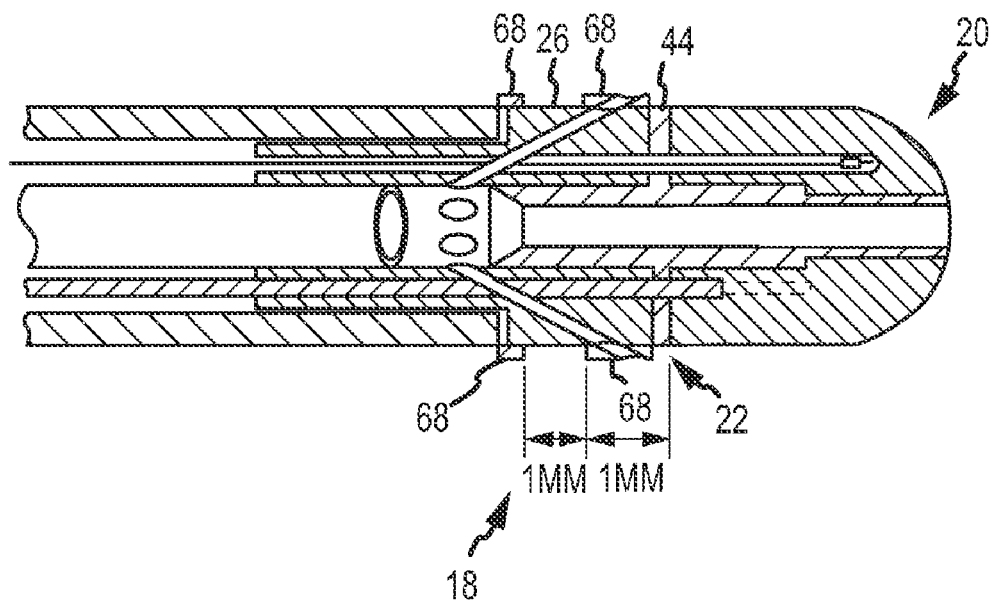
FIG. 11 is a side cross-section view of an alternate embodiment of the present invention.

Lastly, as can be seen in FIG. 11, if the design of proximal member 18 requires a longer length, i.e. a longer outer surface 26, both the distal portion and proximal portion of outer surface 26 of proximal member 18 may be covered with electrical insulation coating 68. A combination of electrical insulation coatings 68 provided on the proximal portion and distal portion of outer surface 26 of proximal member 18 ensure that electrode assembly 10 meets the requirements of catheter assembly 12. As a result the exposed length of proximal member 18 is approximately 1 millimeter, therein providing a sensing electrode and the electrode spacing formed by the combination of electrical insulation coating 68 on the distal portion of outer surface 26 with outer surface 44 of intermediate member 22 is approximately 1 millimeter in length. Overall, the present invention provides a design such that the advantages of the thermally and electrically insulated ablation electrode is able to meet the catheter requirements such a desirable sensing electrode length and approximate electrode spacing.

Although a number of embodiments of this invention have been described above with a certain degree of particularity, those skilled in the art could make numerous alterations to the disclosed embodiments without departing from the spirit or scope of this invention. Other embodiments and uses of the devices and method of the present invention will be apparent to those skilled in the art from consideration of the specification and practice of the invention disclosed therein.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An insulated irrigated ablation electrode assembly comprising:
    a proximal member having a body portion including an outer surface, an inner cavity within the body portion, and at least one passageway that extends from the inner cavity to the outer surface of the body portion;
    a distal member having a distal end and an outer surface; and
    an intermediate member including an outer surface, the intermediate member disposed between and separate from both the proximal member and the distal member thereby thermally insulating the proximal member from the distal member, wherein the intermediate member is directly connected to both the proximal member and the distal member,
    wherein the proximal member is configured to receive at least a first portion of the intermediate member such that the first portion of the intermediate member is disposed internally relative to the proximal member, and
    wherein the outer surface of the proximal member, at least a portion of the outer surface of the distal member, and the outer surface of the intermediate member are substantially radially aligned.

2. The electrode assembly of claim 1, wherein the proximal member is comprised of an electrically conductive material.

3. The electrode assembly of claim 2, wherein the electrically conductive material of the proximal member is selected from the group consisting of gold, platinum, iridium, palladium, stainless steel, and combinations thereof.

4. The electrode assembly of claim 1, wherein the proximal member comprises a plurality of passageways disposed circumferentially about the body portion, and wherein the passageways extend from the inner cavity to the outer surface of the body portion.

5. The electrode assembly of claim 4, wherein the passageways extend towards the distal member such that a line extending through the passageway forms an acute angle with a longitudinal axis of the electrode assembly.

6. The electrode assembly of claim 1, wherein the distal member is comprised of an electrically conductive material.

7. The electrode assembly of claim 1, wherein the distal member further comprises an irrigation channel extending through the distal member to the distal end.

8. The electrode assembly of claim 1, wherein a thermal sensor is disposed within the distal member.

9. The electrode assembly of claim 1, wherein the intermediate member is a thermal insulator comprised of a reduced thermally conductive material selected from the group consisting of polyether ether ketone, HDPE, polyimides, polyaryletherketones, polyetheretherketones, polyurethane, polypropylene, oriented polypropylene, polyethylene, crystallized polyethylene terephthalate, polyethylene therephthalate, polyester, polyetherimide, acetyl, ceramics, and combinations thereof.

10. The electrode assembly of claim 1, wherein the intermediate member further provides a distal passageway that is disposed within an irrigation channel provided within the distal member such that the distal passageway that extends from the inner cavity of the proximal member to the distal end of the distal member.

11. The electrode assembly of claim 1, wherein the intermediate member includes an outer surface that provides approximately 1 millimeter of spacing between the proximal member and the distal member of the electrode assembly.

12. The electrode assembly of claim 1, wherein an electrical insulation coating is further provided on a portion of the outer surface of the proximal member.

13. The electrode assembly of claim 12, wherein the electrical insulation coating is comprised of an electrically nonconductive material.

14. The electrode assembly of claim 13, wherein the electrically nonconductive material is selected from diamond, carbon having diamond-like characteristics, polytetrafluoroetheylene (PTFE), or combinations thereof.

15. The electrode assembly of claim 1, wherein the proximal member includes a sensing electrode.

16. The electrode assembly of claim 1, wherein the a pull wire is connected or attached to the proximal member for controlling the deflection of the electrode assembly.

17. The electrode assembly of claim 12 wherein the combined length of the electrical insulation coating disposed on the proximal member and of the intermediate member is approximately 1 millimeter in length.

18. The electrode assembly of claim 1, wherein an electrical insulation coating is further provided on both a proximal portion of the proximal member and on a distal portion of the proximal member such that the combined length of the electrical insulation coating disposed on the distal portion of the proximal member and of the intermediate member is approximately 1 millimeter in length.

19. An insulated irrigated ablation electrode assembly comprising:
    a proximal member having a body portion including an outer surface, an inner cavity defined within the body portion, at least one passageway that extends from the inner cavity to the outer surface of the body portion, and an electrical insulation coating disposed on the outer surface of the body portion;
    a distal member having a distal end and an outer surface; and
    an intermediate member including an outer surface, the intermediate member disposed between and separate from both the proximal member and the distal member thereby thermally insulating the proximal member from the distal member, wherein the intermediate member is directly connected to both the proximal member and the distal member, wherein the proximal member is configured to receive at least a first portion of the intermediate member such that the first portion of the intermediate member is disposed internally relative to the proximal member, and wherein the outer surface of the proximal member, at least a portion of the outer surface of the distal member, and the outer surface of the intermediate member are substantially radially aligned.

20. The electrode assembly of claim 19, wherein the proximal member comprises a plurality of passageways disposed circumferentially about the body portion, and wherein the passageways extend from the inner cavity to the outer surface of the body portion.

21. The electrode assembly of claim 19, wherein the proximal member includes a sensing electrode.

22. The electrode assembly of claim 19 wherein the electrical insulation coating is comprised of an electrically non-conductive material.

23. The electrode assembly of claim 19 wherein the combined length of the electrical insulation coating disposed on the proximal member and of the intermediate member is approximately 1 millimeter in length.

24. The electrode assembly of claim 19, wherein the electrical insulation coating is further provided on both a proximal portion of the proximal member and on a distal portion of the proximal member such that the combined length of the electrical insulation coating disposed on the distal portion of the proximal member and of the intermediate member is approximately 1 millimeter in length.

25. An irrigated catheter assembly comprising:
a catheter including a catheter shaft having a fluid lumen; and
an insulated irrigated ablation electrode assembly including
a proximal member having a body portion including an outer surface, an inner cavity defined within the body portion, and at least one passageway that extends from the inner cavity to the outer surface of the body portion;
a distal member having a distal end and an outer surface; and
an intermediate member including an outer surface, the intermediate member disposed between and separate from both the proximal member and the distal member thereby thermally insulating the proximal member from the distal member, wherein the intermediate member is directly connected to both the proximal member and the distal member, wherein the proximal member is configured to receive at least a first portion of the intermediate member such that the first portion of the intermediate member is disposed internally relative to the proximal member, and wherein the outer surface of the proximal member, at least a portion of the outer surface of the distal member, and the outer surface of the intermediate member are substantially radially aligned.

26. The electrode assembly of claim 1, wherein a portion of the proximal member including the at least one passageway comprises a first material and wherein the intermediate member comprises a second material, wherein the first material and the second material are different.

27. The electrode assembly of claim 1, wherein the first portion of the intermediate member has a first outer surface having a first outer diameter and wherein the intermediate member comprises a second portion having a second outer surface having a second outer diameter, wherein the first outer diameter is smaller than the second outer diameter.

28. The electrode assembly of claim 27, wherein the intermediate member further comprises a third portion having a third outer surface having a third outer diameter, wherein the third outer diameter is smaller than the second outer diameter, wherein the distal member is configured to receive at least the third portion of the intermediate member such that the third portion of the intermediate member is disposed internally relative to the distal member, and wherein at least the third portion of the intermediate member comprises a distal passageway that is disposed within an irrigation channel provided within the distal member such that the distal passageway extends from the inner cavity of the proximal member to the distal end of the distal member.

* * * * *